United States Patent [19]
Williams, III

[11] Patent Number: 4,891,756
[45] Date of Patent: Jan. 2, 1990

[54] NUTRITIONAL MICROCOMPUTER AND METHOD

[76] Inventor: William B. Williams, III, 946 Montgomery Ave., Albemarle, N.C. 28001

[21] Appl. No.: 248,608

[22] Filed: Sep. 26, 1988

[51] Int. Cl.⁴ .............................................. G06F 15/40
[52] U.S. Cl. ........................... 364/413.29; 364/709.02
[58] Field of Search ....................... 364/413.29, 715.15, 364/709.02, 200 MS File, 900 MS File

[56] References Cited

U.S. PATENT DOCUMENTS

| | | | |
|---|---|---|---|
| 4,244,020 | 1/1981 | Ratcliff | 364/413.29 |
| 4,321,674 | 3/1982 | Krames et al. | 364/413.29 |
| 4,380,802 | 4/1983 | Segar | 364/900 |
| 4,575,804 | 3/1986 | Ratcliff | 364/413.29 |
| 4,686,624 | 8/1987 | Blum et al. | 364/413.29 |
| 4,796,182 | 1/1989 | Duboff | 364/413.29 |

FOREIGN PATENT DOCUMENTS 146356  8/1985  Japan ............................... 364/413.29

OTHER PUBLICATIONS

"Improving Diet, Byte by Byte", S. Squires, Washington Post, Jan. 30, 1985.

*Primary Examiner*—Jerry Smith
*Assistant Examiner*—Steven Kibby
*Attorney, Agent, or Firm*—Daniel E. McConnell

[57] ABSTRACT

This invention relates to a microcomputer and method for selecting foodstuffs and maintaining a record of the nutritional values of foodstuffs eaten. The apparatus has a memory for receiving and retaining a data base of information regarding foodstuffs, accessing keys for accessing from the memory foodstuff identifying information regarding a selected class of foodstuffs from among those in the data base, a display for displaying a plurality of lines of information for a correponding plurality of foodstuffs accessed from the memory, selection keys for selecting from the display of a plurality of lines of information that foodstuff identifying and nutritional value information which relates to a specific foodstuff, and a register for registering the information selected from the display regarding a specific foodstuff and for accumulating over an interval of time the information regarding additional selected foodstuffs.

33 Claims, 3 Drawing Sheets

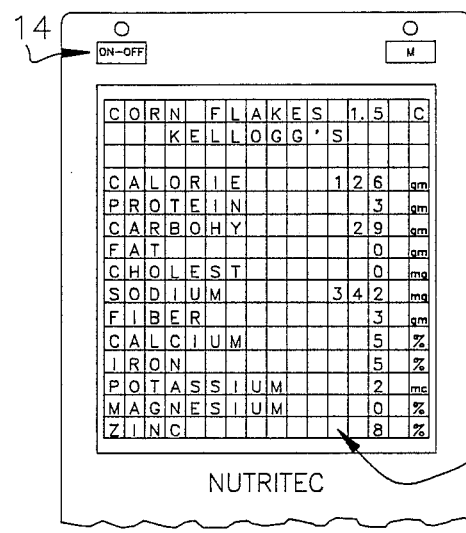
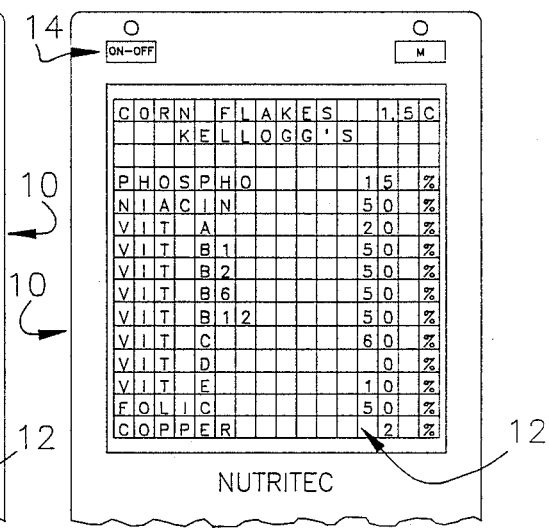
FIG.6  FIG.7
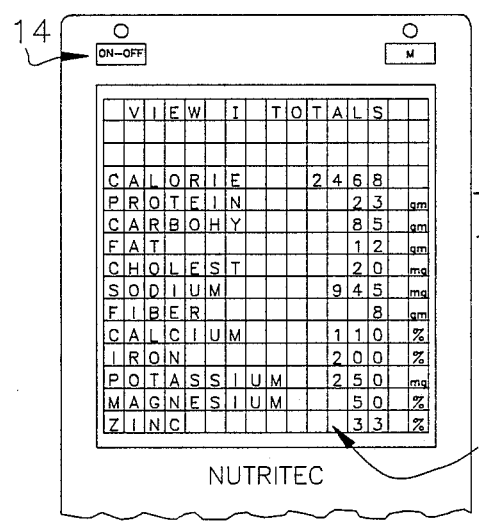
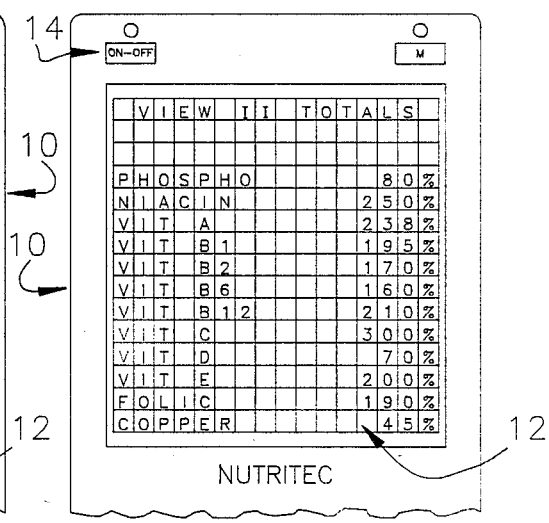
FIG.8  FIG.9

NUTRITIONAL MICROCOMPUTER AND METHOD

FIELD AND BACKGROUND OF INVENTION

This invention relates to a microcomputer and method for selecting foodstuffs and maintaining a record of the nutritional values of foodstuffs eaten.

Many persons must select foods to eat based upon dietary restrictions imposed by desired weight control or by physician's prescriptions for maintaining health. Many aids have been proposed for persons engaged in such selection and recording of foodstuffs eaten, including at least some computerized record keeping schemes as shown, for example, in Ratcliff U.S. Pat. Nos. 4,244,020; Krames 4,321,674; Segar 4,380,802; Ratcliff 4,575,804; and Blum 4,686,624.

Such devices and methods as known prior to the present invention suffer from a number of difficulties and deficiencies. Most notable are limitation on the number of specific foodstuffs which can be considered, the types of nutritional values which can be noted and recorded, and the correlation of the nutritional values with known branded products. For example only, while a person on a restricted diet may well consider eating a McDonald's hamburger (and such may be entirely permissible within the scope of any self imposed or prescribed diet), there is no reasonable way provided by the prior devices and methods to evaluate with any accuracy the effect on an overall dietary plan of such a branded product. Indeed, many prior devices and methods start from the assumption that the user already knows the nutritional values of such foodstuffs or can at the least closely approximate them. Such devices and methods are of limited usefulness to a person who finds themselves frequently in commercial establishment where foodstuff make-up and quantities are controlled by the food provider and not by the consumer.

BRIEF DESCRIPTION OF INVENTION

With the foregoing in mind, it is an object of this invention to provide an apparatus and method enabling a person who chooses to exercise care in selecting a diet to be well advised regarding the nutritional values of foodstuffs available for consumption. In realizing this object of the present invention, a hand held microcomputer is contemplated in which a data base of information regarding a large number of possible foods to be eaten is maintained in a form organized to permit ease of access to the information. More particularly, nutritional information is organized within the data base by groupings of foodstuffs by type and, in some regards, by source.

Yet a further object of this invention is to enable a user of the apparatus contemplated by this invention to view information regarding a number of foodstuffs by progression through groupings displayed and organized to permit access first to a plurality of types of foods, then to a plurality of foods within a common group, and then to detailed nutritional information about a specific selected food. In realizing this object of the present invention, data regarding a number of foods is entered into and maintained in a data base having a particular hierarchic structure.

Yet a further object of this invention is permit a user of the present invention to accumulate a record over time of the nutritional values ingested. In realizing this object of the present invention, provision is made for registering the information related to a specific selected foodstuff and accumulating over time the information relating to the series of foods selected over that interval.

BRIEF DESCRIPTION OF DRAWINGS

Some of the objects of the invention having been stated, other objects will appear as the description proceeds, when taken in connection with the accompanying drawings, in which:

FIGS. 2 through 9 are a series of essentially similar views, all elevations views of a portion of the apparatus of FIG. 1, showing the display screen with a series of messages displayed which illustrate the operation of the apparatus of this invention.

DETAILED DESCRIPTION OF INVENTION

Figure 1:
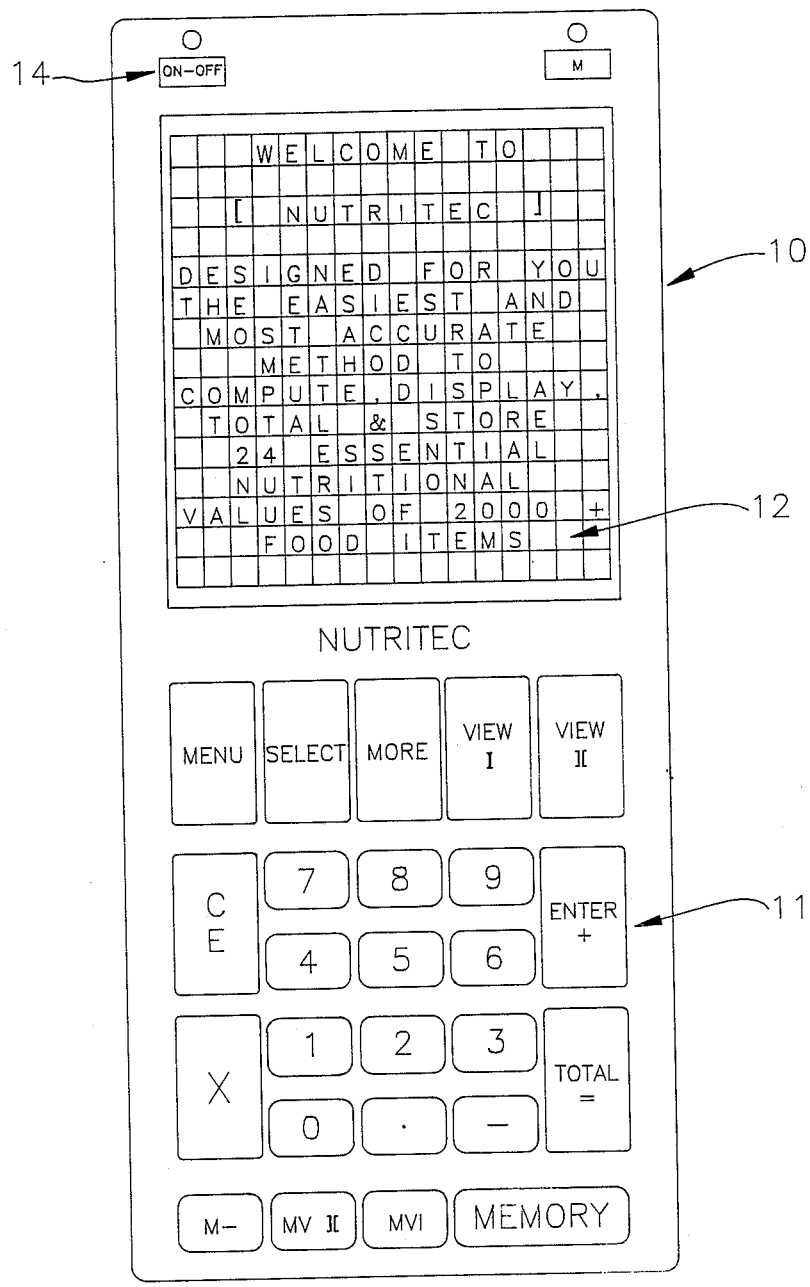
FIG. 1 is an elevation view of the apparatus of this invention, showing the display screen with a introductory message displayed.

While the present invention will be described more fully hereinafter with reference to the accompanying drawings, in which a preferred embodiment of the present invention is shown, it is to be understood at the outset of the description which follows that persons of skill in the appropriate arts may modify the invention here described while still achieving the favorable results of this invention. Accordingly, the description which follows is to be understood as being a broad, teaching disclosure directed to persons of skill in the appropriate arts, and not as limiting upon the present invention.

Referring now more particularly to the accompanying drawings, the apparatus of the present invention is there shown and generally identified at 10. The series of views included in the drawings, and the description of those views which follows, relate primarily to the messages displayed as the use of the apparatus proceeds. The specific microcomputer chips or elements used to accomplish the purposes which will become more clear as the description proceeds, and the manner of interconnecting those elements, are not shown in detail in the drawings, and specific suggestions for such elements will not be given in the description. One reason for this is that the technology available for hand held microcomputers changes very swiftly, and that which might be used at the time of development of a commercial embodiment of this invention will differ (sometimes markedly) from that available only months later. Another reason is that any person of average skill in the design and application of computer circuitry and software will be able, after understanding the disclosure of the functions, purposes and methods which follows, to select available and suitable elements and construct an operating embodiment of the present invention. By way of only one example, memory chips capable of retaining the digitally stored information which defines the data base of nutritional information are available in a range of types, capacities and response times. A capable computer design engineer will be able to select those which represent the most reasonable choice at any given time after studying the disclosure which follows. The same conclusion applies with regard to such elements as the display, keyboard, and so forth.

This invention is a nutritional microcomputer apparatus 10 which has suitable memory means in the form of microchips or microcircuits for receiving and retaining a data base of information regarding foodstuffs. An accessing means is provided for accessing from the memory foodstuff identifying information regarding a selected class of foodstuffs from among those in the data base. The accessing means preferably takes the form of certain keys on a suitable keyboard 11, which can be of a conductive elastomeric material, a thin film, or some other known keyboard as used on hand held calculators and the like. A display, preferably a liquid crystal display or LCD indicated at 12, is provided for displaying a plurality of lines of information for a corresponding plurality of foodstuffs accessed from the memory by the accessing keys as described more fully hereinafter. When a display is presented, still other keys of the keyboard 11 function as a selection means for selecting from the display of a plurality of lines of information that foodstuff identifying and nutritional value information which relates to a specific foodstuff, as described hereinafter. Finally, the apparatus 10 includes a register means for registering the information selected from the display regarding a specific foodstuff and for accumulating over an interval of time the information regarding additional selected foodstuffs. The register means may take the form of memory chips as to which power (and thus memory) is continued even while other elements of the microcomputer are unpowered.

It is desirable, in accordance with this invention, that the data base of information stored in the memory include information on the caloric, protein, carbohydrate, fat, sodium, cholesterol, fiber, vitamin and mineral content of foodstuffs. This information is entered into and retained in the data base in correlation to specific brand names of food products, such as Kellogg's brand corn flakes and other cereals, and in correlation to specific servings sizes, such as one cup of cereal.

On activating the apparatus, a user may press the on-off key 14 in the upper left corner of the device illustrated, causing a light emitting diode adjacent the key to be illuminated and the welcome screen shown in FIG. 1 to be displayed.

Figures 2, 3:
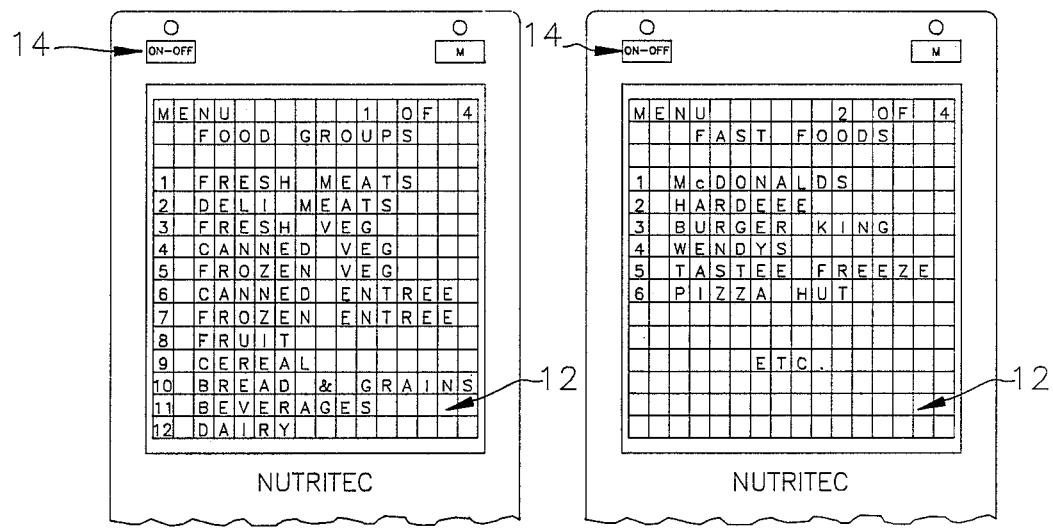

In accessing information from the data base, a user will first select from among the information retained in memory those elements of information which relate to a selected group of related foodstuffs, as by pressing the "MENU" key and causing a display such as that of FIG. 2, which shows the first of four (in the illustrated embodiment) available screens of information. Then using the numeric keypad, the user may select a specific group (such as cereals by pressing the key for the numeral 9 and the "SELECT" key) to reach a display of that specific group (as in FIG. 4). Alternatively, the user may press the key identified by "MORE" to view additional screens of information, including a screen (FIG. 3) which accesses a portion of the data base identifying "fast foods" and containing data on standardized products offered by franchised food operators. Thus the "MENU", "MORE" and "SELECT" keys function as portions of the accessing means.

If at any point in the selection process the user presses a key by error, then the user may simply press the "CE" or "Clear Error" key to return to the last previous screen without continuing an erroneous entry.

Figures 4, 5:
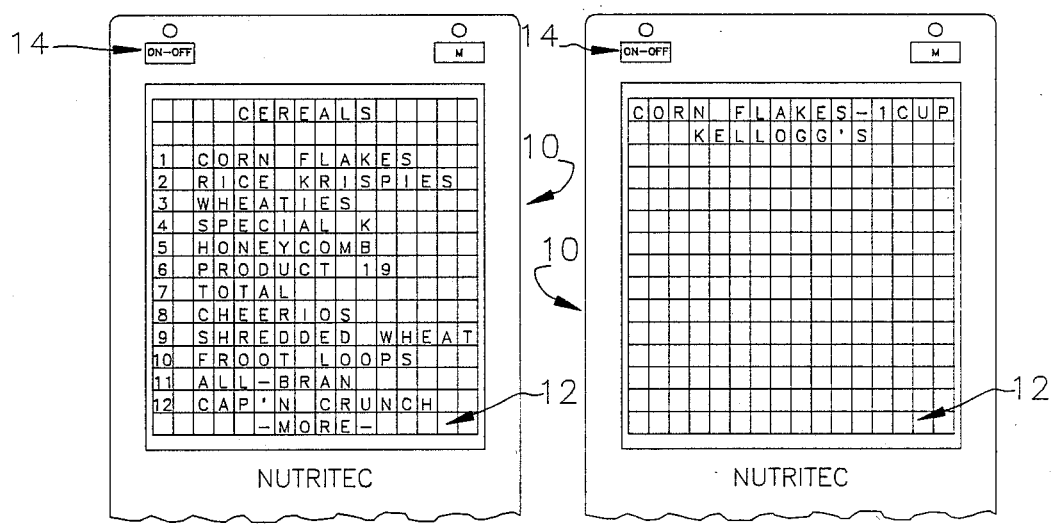

As will be noted, the display 12 displays a predetermined number of lines of information each having a predetermined number of characters. The accessing means is capable of causing the display of foodstuff identifying information absent nutritional value information, as indicated in FIG. 5, where the keypad has been used to select corn flakes and the screen indicates that further indications will be for a quantity of one cup.

At this point in the selection, a user may alter the quantity and/or may view the nutritional values for the standard measure included in the data base. The example here being discussed will have in the data base information regarding the standard quantity of one cup, and variation from that information related to changes in quantity are accomplished by simple programmed division or multiplication. For example, the quantity of food to be considered may be increased to one and one half cups of corn flakes by using the multiplication or "X" key and the numeric keypad to enter 1.5 and the "ENTER" key to cause the multiplication. As anyone familiar with a hand held calculator will understand, the factor by which a food quantity may be varied may be (within reason) any multiplier which can be entered through the keypad.

Once a quantity has been determined, a user may view the particular nutritional values for the selected food and serving size by pressing the "VIEW I" and "VIEW II" keys. In the illustrated embodiment, "VIEW I" brings up a display of calories, protein, carbohydrate, etc. as shown in FIG. 6. "VIEW II", in the illustrated embodiment, is used for vitamins and certain minerals, as shown in FIG. 7. As there illustrated, the values displayed are for the single, selected foodstuff such as cornflakes.

Selection in this manner will enable a user to view, in advance of consuming a particular food, the nutrients available in a selected serving size and thereby make a decision about consuming that food or varying a serving size to be selected.

The present invention contemplates that, after selecting a particular food and serving size, a user will register the nutritional values by pressing the "ENTER" or "+" key, causing the nutritional values of the selected food and serving size to be registered in an ongoing memory. Alternatively, should the user have entered into the register a food which was not in fact eaten, or which was actually consumed in a smaller serving size, then a comparable selection process followed by pressing the minus or "−" key will subtract the nutritional values from the ongoing register.

In order to provide for viewing the nutritional effect of an entire meal, the user may enter the values of selected food and servings into a meal register by pressing the "TOTAL" key, and then view and adjust the meal register amounts as required to achieve particular nutritional targets. Once an entire meal has been determined with finality, the user may press the "MEMORY" key and cause the totals in the meal register to be transferred to a long term register, such as a daily register. Pressing the "MEMORY" key will return the screen display to the introductory message of FIG. 1. The summed totals retained in the meal or longer term registers may be accessed by pressing the key "MVI" for viewing the memory of values represented in the "VIEW I" screen and table and the key "MVII" for view those represented in the "VIEW II" screen (FIGS. 8 and 9).

It is anticipated that, in use, the apparatus will come into the hand of a user with the data base of information entered and stored in memory which is inaccessible for change by the user. However, it is contemplated that the number of food items which can be accommodated by the "tree" structure of the data base can easily be on the order of twenty thousand, and thus ample to accommodate the tastes of substantially any user.

In the drawings and specifications there has been set forth a preferred embodiment of the invention and, although specific terms are used, the description thus given uses terminology in a generic and descriptive sense only and not for purposes of limitation.

What is claimed is:

1. A nutritional microcomputer apparatus comprising:
    memory means for receiving and retaining a data base of information regarding foodstuffs,
    accessing means for accessing from said memory means foodstuff identifying information regarding a selected group of foodstuffs from among those in the data base,
    display means for displaying a plurality of lines of information for a corresponding plurality of foodstuffs accessed from said memory means by said accessing means,
    selection means for selecting from the display of a plurality of lines of information that foodstuff identifying and nutritional value information which relates to a specific foodstuff, and
    register means for registering the information selected from the display regarding a specific foodstuff and for accumulating over an interval of time the information regarding additional selected foodstuffs.

2. Apparatus according to claim 1 wherein said memory means retains information regarding the caloric content of foodstuffs.

3. Apparatus according to claim 1 wherein said memory means retains information regarding the protein content of foodstuffs.

4. Apparatus according to claim 1 wherein said memory means retains information regarding the carbohydrate content of foodstuffs.

5. Apparatus according to claim 1 wherein said memory means retains information regarding the fat content of foodstuffs.

6. Apparatus according to claim 1 wherein said memory means retains information regarding the sodium content of foodstuffs.

7. Apparatus according to claim 1 wherein said memory means retains information regarding the cholesterol content of foodstuffs.

8. Apparatus according to claim 1 wherein said memory means retains information regarding the fiber content of foodstuffs.

9. Apparatus according to claim 1 wherein said memory means retains information regarding at least one mineral contained in the foodstuffs.

10. Apparatus according to claim 1 wherein said memory means retains information regarding at least one vitamin contained in the foodstuffs.

11. Apparatus according to claim 1 wherein said memory means retains information regarding the brand names of specific foodstuff products.

12. Apparatus according to claim 1 wherein said memory means retains information regarding the serving size of foodstuffs.

13. Apparatus according to claim 1 wherein said accessing means selects, on repeated actuation, from among the information retained in said memory means those elements of information which relate to a series of selected groups of related foodstuffs, each group being displayed as actuation of said accessing means is repeated.

14. Apparatus according to claim 1 wherein said display means displays a predetermined number of lines of information each having a predetermined number of characters and further wherein said accessing means causes the display of foodstuff identifying information absent nutritional value information.

15. Apparatus according to claim 14 wherein said selection means causes the display of foodstuff identifying and nutritional value information for a single selected foodstuff.

16. Apparatus according to claim 1 wherein said register means accumulates totals of nutritional values for selected foodstuffs over daily intervals.

17. A nutritional microcomputer apparatus comprising:
    memory means for receiving and retaining a data base of foodstuff identifying and nutritional value information regarding a plurality of classes of foodstuffs, the nutritional value information comprising information on content of calories, protein, carbohydrate, fat, sodium, cholesterol, fiber, at least one mineral and at least one vitamin,
    accessing means for accessing from said memory means foodstuff identifying information regarding one selected group of foodstuffs from among those in the data base,
    display means for displaying a plurality of lines of foodstuff identifying information for a corresponding plurality of foodstuffs accessed from said memory means by said accessing means,
    selection means for selecting from the display of a plurality of lines of information that foodstuff identifying and nutritional value information which relates to a specific foodstuff, and
    register means for registering the information selected from the display regarding a specific foodstuff and for accumulating over a day the information regarding selected foodstuffs.

18. A method of recording the nutritional values of foodstuffs selected for consumption and comprising the steps of:
    entering into and retaining in a data base memory information regarding nutritional values for a plurality of groups of foodstuff types each comprising a number of individual foodstuffs,
    accessing from the data base memory foodstuff identifying information regarding a selected group of foodstuffs from among those in the data base,
    displaying a plurality of lines of information for a corresponding plurality of foodstuffs accessed from the data base memory means,
    selecting from the display of a plurality of lines of information that foodstuff identifying and nutritional value information which relates to a specific foodstuff, and
    registering the information selected from the display regarding a specific foodstuff and accumulating over an interval of time the information regarding additional selected foodstuffs.

19. A method according to claim 18 wherein said steps of entering into and retaining in a data base memory and registering information include entering information regarding the caloric content of foodstuffs.

20. A method according to claim 18 wherein said steps of entering into and retaining in a data base memory and registering information include entering information regarding the protein content of foodstuffs.

21. A method according to claim 18 wherein said steps of entering into and retaining in a data base memory and registering information include entering information regarding the carbohydrate content of foodstuffs.

22. A method according to claim 18 wherein said steps of entering into and retaining in a data base memory and registering information include entering information regarding the fat content of foodstuffs.

23. A method according to claim 18 wherein said steps of entering into and retaining in a data base memory and registering information include entering information regarding the sodium content of foodstuffs.

24. A method according to claim 18 wherein said steps of entering into and retaining in a data base memory and registering information include entering information regarding the cholesterol content of foodstuffs.

25. A method according to claim 18 wherein said steps of entering into and retaining in a data base memory and registering information include entering information regarding the fiber content of foodstuffs.

26. A method according to claim 18 wherein said steps of entering into and retaining in a data base memory and registering information include entering information regarding the mineral content of foodstuffs.

27. A method according to claim 18 wherein said steps of entering into and retaining in a data base memory and registering information include entering information regarding the vitamin content of foodstuffs.

28. A method according to claim 18 wherein said steps of entering into and retaining in a data base memory and registering information include entering information regarding the brand names of specific foodstuff products.

29. A method according to claim 18 wherein said steps of entering into and retaining in a data base memory and registering information include entering information regarding the serving size of foodstuffs.

30. A method according to claim 18 wherein said step of accessing identifying information selects from among the information retained in the data base memory those elements of information which relate to a selected group of related foodstuffs.

31. A method according to claim 18 wherein said step of accessing identifying information comprises selecting, on repeated actuation, from among the information retained in said memory means those elements of information which relate to a series of selected groups of related foodstuffs, each group being displayed as actuation of an accessing key is repeated.

32. A method according to claim 18 wherein said step of accessing information causes the display of foodstuff identifying and nutritional value information for a single selected foodstuff.

33. A method according to claim 18 wherein said step of registering comprises accumulating totals of nutritional values for selected foodstuffs over daily intervals.

* * * * *